United States Patent [19]

Tanner

[11] 4,409,102
[45] Oct. 11, 1983

[54] PROCESS FOR REMOVING CONTAMINANTS FROM A STREAM OF METHANE GAS

[75] Inventor: Milton R. Tanner, Whittier, Calif.

[73] Assignee: Central Plants, Inc., Culver City, Calif.

[21] Appl. No.: 325,327

[22] Filed: Nov. 27, 1981

[51] Int. Cl.³ .................... C02F 11/04; B01D 53/26
[52] U.S. Cl. ........................... 210/603; 55/31; 55/33; 55/48; 55/73; 423/231
[58] Field of Search ............ 55/30, 31, 33, 48, 73; 210/603, 604; 423/230, 231

[56] References Cited

U.S. PATENT DOCUMENTS

| | | | |
|---|---|---|---|
| 1,907,579 | 5/1933 | Quelch | 55/30 X |
| 2,033,933 | 3/1936 | Goodwin et al. | 423/231 X |
| 2,097,454 | 11/1937 | Fischer | 55/73 X |
| 2,208,029 | 7/1940 | Heckman | 423/231 X |
| 2,378,689 | 6/1945 | Collins | 423/230 |
| 2,541,630 | 2/1951 | Yeomans | 210/603 |
| 2,780,310 | 2/1957 | Schaub | 55/73 |
| 2,881,137 | 4/1959 | Logan | 210/603 |
| 2,983,573 | 5/1961 | Moore et al. | 423/231 |
| 3,847,570 | 11/1974 | Gunther | 55/73 |
| 3,973,043 | 8/1976 | Lynn | 210/603 X |
| 3,981,800 | 9/1976 | Ort | 210/603 |
| 4,000,990 | 1/1977 | Bingham | 55/30 |
| 4,123,355 | 10/1978 | Poradek et al. | 55/73 X |
| 4,157,958 | 6/1979 | Chow | 210/603 |

OTHER PUBLICATIONS

Bloodgood, "Gas From Sewage Sludge," Water & Sewage Works, Nov. 1954, pp. 512-514.

Primary Examiner—Robert H. Spitzer
Attorney, Agent, or Firm—Christie, Parker & Hale

[57] ABSTRACT

A feed stream of digester gas from an anaerobic process is compressed to a predetermined pressure of about 300 p.s.i.g. and fed into an absorber at that pressure. Carbon dioxide and hydrogen sulfide impurities of this feed stream are absorbed in the absorber by counterflowing water. Water from the absorber may be fed back to an activated sludge sewage treatment facility where the hydrogen sulfide is oxidized and the carbon dioxide released. As an alternative to the absorber, hydrogen sulfide is oxidized in an iron sponge reaction. Alternately, these contaminants are stripped with air and vented. Treated gas from the absorber, essentially methane, is either compressed for introduction into storage tanks, or dried and used as pipeline gas. In the dryer, adsorbed moisture is removed by air, followed by a purge with treated gas.

14 Claims, 1 Drawing Figure

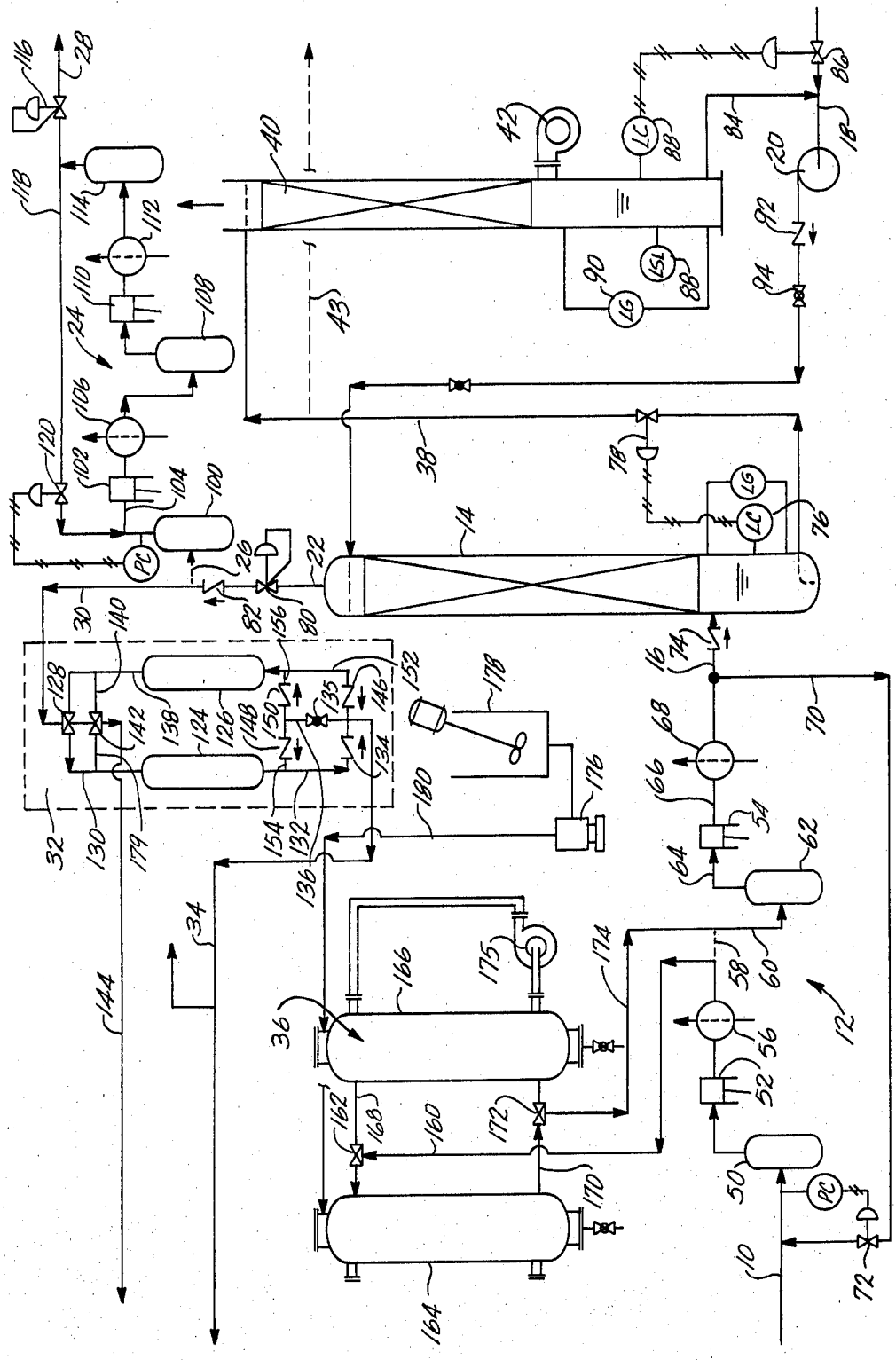

PROCESS FOR REMOVING CONTAMINANTS FROM A STREAM OF METHANE GAS

BACKGROUND OF THE INVENTION

The present invention relates in general to the purification of gases, and, in particular, to the concentration of methane from a gas feed stream.

Methane comes from a variety of reactions. Methane is a good fuel gas, it being the major constituent of natural gas. Examples of sources of methane gas include biological degradation of sewage waste or digester gas, foodstuff waste, animal feed lot waste, and land fills. Interest in these sources of methane gas has heightened because of the energy crisis.

Typical gaseous products from these sources are heavily contaminated with carbon dioxide and hydrogen sulfide. Hydrogen sulfide must be removed because of its toxicity and odor. Carbon dioxide reduces the heating value of the gas and it is desirable to remove it for that reason. In some applications the value of the gas must be comparatively high to merit the gas's use.

One proposed use for concentrated methane from these sources is as a fuel for automobiles. The gas is stored in high pressure storage tanks, at a pressure of up to 3,600 p.s.i.g. The stored gas is then transferred to high pressure storage tanks of vehicles to pressures up to about 3,000 p.s.i.g. Vehicles can be filled directly, bypassing storage.

Another proposed use of the methane is as pipeline gas. The reclaimed methane of adequate quality is introduced into utility provided natural gas to augment that supply.

It is known that carbon dioxide and hydrogen sulfide can be absorbed from methane by passing the stream containing the three gases countercurrent to water. The water absorbs the carbon dioxide and hydrogen sulfide. It is also known that the residence time of the gas stream in contact with the water and the quantity of water affect resulting purity; the more water, the higher the effluent stream's purity; the greater the residence time, the greater the purity. It is also known that residence time can be increased by increasing the height of a column used for the counterflowing process streams. Further, it is known that increases in pressure enhance purity by making the impurities more soluble in water.

It is also known that water containing hydrogen sulfide and carbon dioxide can be freed of those contaminants by stripping with air. Iron sponge reactions where hydrogen sulfide is oxidized to elemental sulfur and water is also known.

To purify streams containing methane, the process should be efficient, reliable, and versatile.

SUMMARY OF THE INVENTION

The present invention provides a method for purifying methane gas of a stream constituted of methane gas, carbon dioxide, and, perhaps, hydrogen sulfide. The present invention effects purification of the stream to get high quality methane by passing the stream to be purified into contact with water to absorb the contaminants. This absorption step is undertaken within a prescribed pressure range corresponding to pressure required for desired purity in view of the limitations of the water flow rate and time of contact of the water stream and the stream being purified. The feed stream is compressed to the pressure at which absorption takes places. No purified gas leaves the system until the pressure in the absorber has been reached and consequential methane purity assured.

In greater detail, the present invention contemplates a system for the purification of a feed stream containing methane, carbon dioxide, and hydrogen sulfide. The feed stream passes countercurrent to water for the absorption of carbon dioxide and hydrogen sulfide from the stream and to produce a stream of methane. Absorption is at an elevated pressure achieved by compression. The absorption takes place in an absorber with the stream to be purified entering the bottom of the absorber. A purified stream of methane exits from the top of the absorber. Countercurrent water enters the absorber at the top and is sprayed against the counterflowing gaseous stream. The purified methane then may be dried and passed from the system. Alternatively, the methane can be compressed to desired discharge pressure, for example, about 3,600 p.s.i.g. Compression before and after absorption may be in stages with interstage cooling. Water used in the absorber may be purified of carbon dioxide and hydrogen sulfide in a scrubber and recycled with the contaminants vented to atmosphere. Where at site oxidation of hydrogen sulfide is necessary, the hydrogen sulfide can be oxidized prior to absorption, as by the iron sponge reaction. Preferably, any such iron sponge reaction occurs between stages of feed gas compression to obtain an appropriate reaction pressure. The scrubber is at considerably lower pressures than the absorber to allow carbon dioxide and any hydrogen sulfide to come out of solution from the water. Countercurrent air then strips the contaminants.

In some instances, the contaminated stream from the absorber is passed directly back into an activated sewage sludge treatment facility where the contaminants are removed from the water.

When the product gas is to be used as pipeline gas, it is preferably dried in an adsorber. The adsorbers may be regenerated by air. To maintain product gas quality, the regenerated adsorber is purged of air by-product gas.

The present invention provides a process to reclaim methane from an otherwise uneconomical source. The methane is a substantial constituent in such streams as sewer gas streams, biogas, dairy and poultry operations, and land fill gas reclamation. Typically, these sources of methane also include as contaminants a high percentage of carbon dioxide and hydrogen sulfide. Hydrogen sulfide is a noxious substance and should be removed from any fuel gas. Carbon dioxide materially reduces the heating value of the gas. In one application of the process of the present invention it is proposed to use the resultant gas as a fuel for automobiles. That requires a comparatively high heating value gas for adequate vehicle performance. In addition, fuel storage in a gaseous state is a problem and, accordingly, the heating value in fuel should be high.

These and other features, aspects and advantages of the present invention will become more apparent from the following description, appended claims and drawings.

DESCRIPTION OF THE FIGURE

The single FIGURE is a flow schematic of a preferred embodiment of the present invention.

DESCRIPTION OF THE PREFERRED EMBODIMENTS

An aspect of the present invention is its facility to adapt to many different types of applications, depending on user requirements and environmental dictates.

The present invention takes a gas feed stream, such as gas from an anaerobic digester containing significant amounts of methane and the contaminants of carbon dioxide ($CO_2$) and hydrogen sulfide ($H_2S$) and removes the contaminants. It does so in an absorption process. Generally this process passes the gas stream into a column countercurrent to water and absorbing the contaminants in the water. Absorption efficiency increases with increased pressure in an absorption vessel. The more contact the water and gas have, the more efficient the absorption; thus increasing the height of the absorber increases its efficiency. And increasing the flow rate of the water increases absorber efficiency.

The digester gas will typically have the following quality:

| | |
|---|---|
| Methane | 50 to 75% by volume |
| $CO_2$ | 50 to 25% by volume |
| $H_2S$ | 1,000 to 2,000 p.p.m. (parts per million) |
| $H_2O$ | saturated at 90° F. |

Generally the treated gas quality will be:

| | |
|---|---|
| Methane | About 98% by volume |
| $CO_2$ | Less than 2% by volume |
| $H_2S$ | 4 p.p.m. |
| $H_2O$ | 90 lbs./MMscf at 300 p.s.i.g. and 80° F., or 15 lbs./MMscf at 3,600 p.s.i.g. and 80° F. |

These requirements for gas quality can be met with absorption pressure of about 300 p.s.i.g. Adequate efficiencies are obtained by obtaining about 93% of the methane available from the digester gas feed stream.

With respect to the drawing, a low pressure feed gas stream 10 of digester gas, is compressed in a feed gas compressor 12 to about 300 p.s.i.g. The pressure of the low pressure feed gas stream is typically from zero to 7 inches of water. After compression, the feed gas stream is introduced into an absorber 14 as a stream 16.

Feed water in a stream 18 is pressurized to about 300 p.s.i.g. by a water pump 20 and introduced into the top of the absorber. The water and feed gas pass countercurrent in the absorber. The water absorbs carbon dioxide and any hydrogen sulfide. The feed gas, now treated, leaves the absorber as a treated gas stream in a line 22. In the event that the treated gas is to be used in the charging of gas cylinders, as for the fueling of natural gas operated vehicles, it is passed into treated gas compressor 24 through a line 26. In this second compressor, the treated gas is brought up to a pressure of, say, 3,600 p.s.i.g. The high pressure, treated gas is discharged from compressor 24 and leaves through a line 28.

As an alternative to the second stage of compression, the treated gas can be used as pipeline gas. In this event, the treated gas stream is passed into a line 30 and into gas dryer 32. The dryer has adsorbers that remove the water from the treated gas. The discharge from the dryers is product gas and it leaves the adsorbers in a line 34.

Hydrogen sulfide can be absorbed by the water in absorber 14. Alternatively, the hydrogen sulfide can be removed from the feed gas in iron sponge reactors 36 at an interstage point in the compression of feed gas compressor 12.

When hydrogen sulfide is absorbed in the absorber, it and the carbon dioxide in the water stream from the absorber are passed through a line 38 to the top of a stripper 40. Air introduced by a blower 42 at the bottom of the stripper flows countercurrent to the water. The pressure in the stripper is low and the hydrogen sulfide and carbon dioxide come out of solution. The counterflowing air strips the released hydrogen sulfide and carbon dioxide.

In some applications the air with the contaminants can be vented to atmosphere.

In those applications where venting of hydrogen sulfide to atmosphere is not possible, the iron sponge reactors or some other at-hand system are required. As an example of an at-hand system, digester gas often is associated with water reclamation plants that use an activated sludge sewage treatment process. In the activated sludge sewage treatment process, hydrogen sulfide is oxidized to elemental sulfur, and, therefore, the process can be used to dispose of the hydrogen sulfide. With this alternative, water and its contaminants pass from line 38 into a line 43 that passes to the water treating facility of the activated sludge treatment plant. The makeup water for line 18 may come from such an activated sludge sewage treatment process.

What has been described to this point is a basic system that purifies digester gas of carbon dioxide and hydrogen sulfide and permits the treated gas to be either further compressed for storage in gas containers or used in a pipeline. Hydrogen sulfide is taken out in an iron sponge reactor or an absorber. If the absorber is used, the hydrogen sulfide can be removed in a stripper and vented to atmosphere. Alternatively, with an absorber the hydrogen sulfide can be removed in an activated sludge sewage treatment cycle.

The purification that utilizes the activated sludge sewage treatment process is a once-through system insofar as the water used in the absorber is concerned. With this approach, the only processing equipment that is required when the product is to be used as a pipeline gas is the absorber, compressor 12, water pump 20, and gas dryer 32.

If the product gas in the once-through process is to be used to charge gas cylinders, the dryer is not necessary, but treated gas compressor 24 is necessary.

In those applications with gas venting, the equipment necessary includes the feed gas compressor 12, absorber 14, stripper 40, water pump 20, and, depending on the use of the product gas, either dryer 32 or treated gas compressor 24.

In those applications where oxidation of hydrogen sulfide is necessary, iron sponge reactors 36 must be provided in addition to those pieces of processing equipment used in gas venting.

In greater detail, feed gas stream 10 passes into feed gas compressor 12 downstream from a moisture knockout vessel 50. Vessel 50 may act as a plenum and help to smooth out fluctuations in digester gas supply. Compressor 12 is a two-stage compressor having stages 52 and 54. Interstage cooling is effected by a heat exchanger 56 utilizing cooling water as the cooling media.

When iron sponge reactor vessels 36 are not used, the discharge from heat exchanger 56 passes through a line 58 into a line 60. The gas in line 60 flows into a moisture knockout vessel 62 prior to its introduction through a line 64 into second stage 54 of compressor 12. The discharge of second stage 54 is through a line 66. A heat exchanger 68 cools the gas in line 66. A recycle gas stream tees off of line 66 in line 70. Line 16 joins lines 66 and 70. A pressure control valve 72 in line 70 responds to the pressure in line 10 to open when the pressure there falls below some predetermined limit. The recycle gas passing through a line 70 assures a constant supply of gas for compressor 12 to take into account irregularities in the discharge of digester gas.

Gas flowing in line 16 into absorber 14 does so through a check valve 74 that prevents gas from backflowing out of the absorber and into line 16.

A predetermined range of liquid level is maintained in absorber 14 by a liquid control sensor 76, which may be a float control. Control 76 controls a valve 78 in line 38. When the liquid level in absorber 14 falls below a predetermined point, control 76 notices this fact and closes valve 78. This prevents water flow in line 38 to the stripper or back to the activated sludge cycle of the water supply.

As previously mentioned, the pressure in absorber 14 is maintained at about 300 p.s.i.g. This pressure is maintained through a pressure regulated valve 80 in line 22. When the pressure in line 22 drops below 300 p.s.i.g., valve 80 closes to permit the pressure in the absorber to increase to the 300 p.s.i.g. operating point. A check valve 82 in line 22 prevents backflow of gas to the absorber.

Stripper 40 receives its water and dissolved carbon dioxide and any hydrogen sulfide through line 38. It receives its air through blower 42. The stripper performs its function in a known manner by the countercurrent contact of released carbon dioxide and hydrogen sulfide from descending water with ascending air. Water leaves the stripper in a line 84. Line 84 feeds line 18. A make-up water control valve 86 is in line 18. A liquid level control 88 at the bottom of the stripper assures at least a minimum level of water there. A liquid level gauge 90 may also be used with the absorber as a visual check.

Line 18 downstream of pump 20 has a check valve 92 to prevent reverse flow and depressurization of the absorber during system shutdowns. A flow control valve 94 in line 18 permits adjustment of the water circulation rate into the absorber.

Treated gas compressor 24 is similar to compressor 12 in its use of two stages with interstage cooling and moisture knockout. Gas from absorber 14 enters high pressure compressor 24 at a moisture knockout vessel 100. The discharge of this vessel feeds a first compression stage 102 through a line 104. The discharge from compression stage 102 is cooled by heat exchange with water in a heat exchanger 106. The cooled gas flows into an interstage moisture knockout vessel 108. A second stage of compression 110 is fed by vessel 108. The discharge from the second stage of compression is cooled in a heat exchanger 112 by water and passes into a discharge moisture knockout vessel 114. Line 28 receives gas from plenum 114 via line 118.

A pressure regulator 116 in line 118 establishes the pressure there at the predetermined level of, say, about 3,600 p.s.i.g. In the event that the pressure inlet of stage 102 falls too low, high pressure gas is recycled to the inlet through a line 118. Line 118 has a pressure control valve 120 that opens for this recycling at a predetermined low pressure below the 300 p.s.i.g. absorber pressure. A pressure switch, not shown, may be used to close down the system when the pressure in the tanks being filled reaches the compressor discharge pressure of about 3,600 p.s.i.g.

Dryer 32 includes a pair of adsorbent vessel dryers 124 and 126. The dryers are air dryers. One dryer is on line while the other gives up its moisture to atmosphere. As shown here, adsorber vessel 124 receives a feed through three-way valve 128 and a line 130. Discharge from adsorbent vessel 124 is in line 132 and passes through a check valve 134 in that line to product in line 134. Valve 134 prevents backflow in the direction of the adsorbent vessel. A valve 135 in a line 136 is normally closed to isolate vessel 126 from product gas and dryer feed gas. During this isolation, dryer 126 loses its adsorbed moisture to air by a forced convection system, not shown. When adsorber 126 has been regenerated it may be placed on line but must be purged. For this purpose valve 135 is open and purge gas from adsorber vessel 124 purges the air from vessel 126 through a line 138, a line 140, a three-way valve 142, and a line 144. Line 144 vents the purge gas and air into the atmosphere, to a flare stack, or to some other safe disposal site. After the purge cycle and to put adsorber vessel 126 on line, three-way valves 128 and 142 are actuated to initiate flow in the direction opposite the arrows in the FIGURE, except that there will be no flow through vessel 124 until after regeneration and only during purge. To maintain flow in the proper directions, a series of check valves are provided, comprising check valves 146, 148, 150, and 134 in lines 152, 154, 156 and 132, respectively.

To recapitulate, during the purge of vessel 126, gas flows through lines 136 and 156. When vessel 126 is on line its discharge flows through line 152 and check valve 146 into line 34. During the purge cycle of vessel 124 purge gas flows through line 136 and line 154 through check valve 148 and into the vessel. Purged gas leaves the vessel through line 130, line 179, 3-way valve 142 and line 144.

The iron sponge reactors for removal of $H_2S$ receive their feed of partially compressed feed gas through a line 160. A three-way valve 162 determines which of two iron sponge reaction vessels will be used, vessel 164 or 166. Valve 162 is in a line 168. Iron sponge reactors effect the oxidation of hydrogen sulfide into elemental sulfur and water. A discharge line 170 has a three-way valve 172. That valve directs the discharge into line 174 and hence into line 60 upstream of knockout vessel 62. An iron sponge regeneration blower 175 from vessel 166 prolongs the effectiveness of the iron sponge by mixing it. The blower supplies both vessels through appropriate manifolding. pH control by soda ash injection may be produced through a pump 176 from a soda ash vessel 178. The soda ash can be introduced into the vessels through a line 180.

The present invention has been described with reference to a preferred embodiment. The spirit and scope of the appended claims should not, necessarily, be limited to this description.

What is claimed is:

1. A process for removing contaminants of hydrogen sulfide and carbon dioxide from a low pressure, methane containing feed stream from an anaerobic process comprising:

(a) compressing the feed stream to an intermediate pressure;
(b) removing substantially all the hydrogen sulfide from the feed stream at the intermediate pressure;
(c) compressing the feed stream after the hydrogen sulfide removal step to an absorption pressure that is greater than the intermediate pressure;
(d) absorbing substantially all the carbon dioxide in the stream at the absorption pressure in water in an absorber to produce a treated gas stream;
(e) stripping the carbon dioxide from the water at a pressure lower than the absorption pressure; and
(f) recycling the water into the absorber to absorb further carbon dioxide.

2. The process claimed in claim 1 including the step of compressing the treated gas stream to a pressure adequate to charge high pressure storage tanks.

3. The process claimed in claim 1 including the step of drying the treated gas stream to remove substantially all the moisture.

4. The process claimed in claim 3 wherein the drying step is by adsorption.

5. The process claimed in claim 4 wherein adsorption is effected in at least two air dryer adsorbers, and including the steps of periodically taking each adsorber off line while the other adsorber remains on line and removing the moisture from the off line adsorber by evaporation to atmosphere.

6. The process claimed in claim 1 wherein the compression step is effected in a compressor of at least two stages, and the hydrogen sulfide is removed by oxidizing it in an iron sponge reaction between compression stages.

7. The process claimed in claim 6 wherein the treated gas stream is substantially dried in at least two air dryer adsorbers, and including the steps of periodically taking each adsorber off line while the other adsorber remains on line and removing the moisture from the off line adsorber by evaporation to atmosphere.

8. A process for removing carbon dioxide and hydrogen sulfide from a feed stream containing them and methane comprising the steps of:
(a) forming the feed stream containing hydrogen sulfide, carbon dioxide, and methane from an anaerobic process;
(b) compressing the feed stream to an absorption pressure in a compressor of at least two stages;
(c) removing the hydrogen sulfide from the feed stream by oxidation in an iron sponge reaction between compression stages and at a pressure less than the pressure after the second compression stage; and
(d) absorbing the carbon dioxide in the feed stream at the absorption pressure in water to produce a treated gas stream of primarily methane.

9. The process claimed in claim 8 including the step of compressing the treated gas stream.

10. The process claimed in claim 8 including the step of removing substantially all the water from the treated gas stream.

11. The process claimed in claim 10 wherein the removal step is by adsorption in at least two air dryer adsorbers, and including the steps of periodically and sequentially diverting the treated gas stream from each of the adsorbers and removing the water from the diverted adsorber by evaporation to atmosphere.

12. A process for purifying a feed gas stream of methane, hydrogen sulfide and carbon dioxide by removal of the hydrogen sulfide and carbon dioxide, comprising the steps of:
(a) compressing the feed gas stream to an intermediate pressure;
(b) removing a substantial portion of the hydrogen sulfide from the feed gas stream at the intermediate pressure;
(c) compressing the feed gas stream after the hydrogen sulfide removal step to an absorption pressure that is greater than the intermediate pressure;
(d) absorbing the carbon dioxide from the feed gas stream in an absorber at the absorber pressure in water from a water treatment facility to obtain a treated gas stream;
(e) passing the water with the absorbed hydrogen sulfide and carbon dioxide to the water treatment facility; and
(f) compressing the treated gas stream to a pressure suitable for introduction into high pressure storage tanks.

13. The process claimed in claim 12 including the step of removing substantially all the moisture from the treated gas stream.

14. The process claimed in claim 13 wherein the moisture is removed in at least two air dryer adsorbers, and including the steps of periodically and sequentially taking each adsorber off line and removing its moisture by evaporation into air.

* * * * *